US011068126B2

(12) United States Patent
Zhang et al.

(10) Patent No.: US 11,068,126 B2
(45) Date of Patent: Jul. 20, 2021

(54) METHOD, DEVICE AND SYSTEM FOR AMENDING HEARTBEAT TYPE

(71) Applicant: EDAN INSTRUMENTS, INC., Guangdong (CN)

(72) Inventors: Zaiyang Zhang, Guangdong (CN); Dongxue Shen, Guangdong (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 394 days.

(21) Appl. No.: 15/384,393

(22) Filed: Dec. 20, 2016

(65) Prior Publication Data

US 2018/0059879 A1 Mar. 1, 2018

(30) Foreign Application Priority Data

Aug. 26, 2016 (CN) .......................... 201610728386.7

(51) Int. Cl.
| | |
|---|---|
| *G06F 3/0482* | (2013.01) |
| *A61B 5/0245* | (2006.01) |
| *A61B 5/044* | (2006.01) |
| *A61B 5/00* | (2006.01) |
| *A61B 5/04* | (2006.01) |
| *A61B 5/316* | (2021.01) |
| *A61B 5/339* | (2021.01) |

(52) U.S. Cl.
CPC .......... *G06F 3/0482* (2013.01); *A61B 5/0245* (2013.01); *A61B 5/316* (2021.01); *A61B 5/339* (2021.01); *A61B 5/7475* (2013.01)

(58) Field of Classification Search
CPC ... G06F 3/0482; A61B 5/7475; A61B 5/0245; A61B 5/04012; A61B 5/044

USPC .......................................................... 715/772
See application file for complete search history.

(56) References Cited

U.S. PATENT DOCUMENTS

| | | | | |
|---|---|---|---|---|
| 5,224,486 A | * | 7/1993 | Lerman | ................ A61B 5/7264 600/509 |
| 7,801,594 B1 | * | 9/2010 | Higham | ............... A61B 5/7239 600/515 |

(Continued)

FOREIGN PATENT DOCUMENTS

| | | |
|---|---|---|
| CN | 101991413 A | 3/2011 |
| CN | 102743157 A | 10/2012 |
| JP | 2007000357 A | 1/2007 |

OTHER PUBLICATIONS

Chinese First Office Action, Chinese Application No. 201610728386. 7, dated Aug. 1, 2020 (18 pages).

*Primary Examiner* — Tadesse Hailu
*Assistant Examiner* — Darrin Hope

(57) ABSTRACT

The present disclosure relates to a method, device and system for amending a heartbeat type. The method includes: displaying an interface for presenting heartbeat waveforms; based on a user interface provided on the interface for presenting the heartbeat waveforms, detecting a currently triggered heartbeat type; and when detecting that at least one electrocardiogram waveform on the interface for presenting the heartbeat waveforms is selected, amending a heartbeat type of the selected at least one electrocardiogram waveform as the currently triggered heartbeat type. The technical solutions provided by the present disclosure can simplify operations for amending heartbeat types and thereby improve working efficiency.

14 Claims, 7 Drawing Sheets

(56) References Cited

U.S. PATENT DOCUMENTS

| | | | |
|---|---|---|---|
| 2015/0190068 A1* | 7/2015 | Cole | A61B 5/0456 600/521 |
| 2016/0106332 A1* | 4/2016 | Takeshima | A61B 5/0452 600/521 |
| 2017/0020464 A1* | 1/2017 | Suto | A61B 5/7475 |

* cited by examiner

METHOD, DEVICE AND SYSTEM FOR AMENDING HEARTBEAT TYPE

CROSS-REFERENCE TO RELATED APPLICATIONS

The present application is based upon and claims priority to Chinese Patent Application No. 201610728386.7, filed Aug. 26, 2016, the entire contents of which are incorporated herein by reference.

TECHNICAL FIELD

The present disclosure generally relates to the technical field of ambulatory electrocardiogram examination, and more particularly, to methods, devices and systems for amending a heartbeat type.

BACKGROUND

Ambulatory electrocardiogram examination is one of the most important and irreplaceable examination methods among all existing electrocardiogram examination methods, and has been widely applied in hospitals and medical institutions. The ambulatory electrocardiogram examination method records electrocardiograms under a long lasting active state and can effectively monitor changes in electrocardiograms for a long time period when patients do usual activities. The ambulatory electrocardiogram examination is generally performed by a data recorder and data analysis software. The data recorder samples electrocardiogram signals for a long time period. The sampled electrocardiogram signals or data are analyzed by the data analysis software to give out analysis results. The data sampling time can vary depending on examination requirements, from about 12 to 168 hours, and such long time data sampling can generate 4 to 600,000 electrocardiogram waveforms. In order to guarantee the accuracy of the results, doctors need to quickly view the electrocardiogram waveforms one by one to distinguish heartbeat types of the electrocardiogram waveforms. The numbers of various types of electrocardiogram waveforms are important for determining the results. The data analysis software can help doctors to make initial automatic classifying on the heartbeat signal waveforms and distinguishably display them. In actual applications, doctors need to, according to the initial classification made by the data analysis software, make further judgment on the electrocardiogram waveforms and amend the heartbeat types of electrocardiogram waveforms which are incorrectly determined, so as to guarantee the accuracy of results.

At present, in order to amend heartbeat types, doctors usually skim all electrocardiogram waveforms, and when they find electrocardiogram waveforms, heartbeat types of which are incorrectly determined, they need to amend the heartbeat types of these electrocardiogram waveforms one by one, for example, by clicking a right button of a mouse or by selecting multiple menus, and this need very cumbersome operations. Also, for the electrocardiogram waveforms of the same type which need to be amended, conventional technologies do not provide methods for uniform screening and aggregation and batch processing on these electrocardiogram waveforms, and doctors have to amend the heartbeat types one by one, thereby resulting in repetitive operation and therefore low working efficiency.

It should be noted that, information disclosed in the above background portion is provide only for better understanding of the background of the present disclosure, and thus it may contain information that does not form the prior art known by those ordinary skilled in the art.

SUMMARY

The present disclosure provides methods, devices and systems for amending a heartbeat type, which are capable of simplifying operations for amending heartbeat types and thereby improving working efficiency.

Other characteristics and advantages of the present disclosure will become clear from the following description, or can be partly known by practice of the present disclosure.

According to an aspect of the present disclosure, there is provided a method for amending a heartbeat type, including:

displaying an interface for presenting heartbeat waveforms;

based on a user interface provided on the interface for presenting the heartbeat waveforms, detecting a currently triggered heartbeat type; and when detecting that at least one electrocardiogram waveform on the interface for presenting the heartbeat waveforms is selected, amending a heartbeat type of the selected at least one electrocardiogram waveform as the currently triggered heartbeat type.

According to an implementation of the present disclosure, the user interface includes a control; and wherein the detecting the currently triggered heartbeat type includes:

detecting a heartbeat type input by a user via the control; and determining the heartbeat type input by the user as the currently triggered heartbeat type.

According to another aspect of the present disclosure, there is provided a method for amending a heartbeat type, including:

displaying an interface for presenting heartbeat waveforms;

when detecting that at least one electrocardiogram waveform on the interface for presenting the heartbeat waveforms is selected, based on a user interface provided on the interface for presenting the heartbeat waveforms, detecting a currently triggered heartbeat type; and amending a heartbeat type of the selected at least one electrocardiogram waveform as the currently triggered heartbeat type.

According to an implementation of the present disclosure, the user interface includes an icon for representing a heartbeat type; and wherein the detecting the currently triggered heartbeat type includes:

detecting an icon for representing a heartbeat type which is clicked by a user; and determining the heartbeat type corresponding to the icon as the currently triggered heartbeat type.

According to an implementation of the present disclosure, the method further includes:

according to the currently triggered heartbeat type, storing the selected at least one electrocardiogram waveform into a database associated with the currently triggered heartbeat type.

According to an implementation of the present disclosure, the user interface further includes an input window for inputting heartbeat feature values; and wherein the method further includes:

detecting a heartbeat feature value which is input into the input window by a user;

amending a heartbeat feature value which is preset for the currently triggered heartbeat type as the heartbeat feature value which is input by the user; and recording the heartbeat feature value of the currently triggered heartbeat type as the amended heartbeat feature value.

According to an implementation of the present disclosure, the method further includes:

determining whether a difference value between a heartbeat feature value of the selected at least one electrocardiogram waveform and a heartbeat feature value of the currently triggered heartbeat type is within a preset range; and if the difference value is within the preset range, amending the heartbeat type of the selected at least one electrocardiogram waveform as the currently triggered heartbeat type.

According to an implementation of the present disclosure, the method further includes:

according to one of electrocardiogram waveforms which are currently selected and heartbeat types of which are amended, searching other electrocardiogram waveforms which have the same heart beat feature value as that of the selected one on the interface for presenting heartbeat waveforms, and amending the heartbeat types of the other electrocardiogram waveforms as the currently triggered heartbeat type.

According to another aspect of the present disclosure, there is provided a system for amending a heartbeat type, including:

a processor; and a memory for storing instructions executable by the processor;

wherein the processor is configured to execute the instructions to:

display an interface for presenting heartbeat waveforms;

based on a user interface provided on the interface for presenting the heartbeat waveforms, detect a currently triggered heartbeat type; and when detect that at least one electrocardiogram waveform on the interface for presenting the heartbeat waveforms is selected, amend a heartbeat type of the selected at least one electrocardiogram waveform as the currently triggered heartbeat type.

According to an implementation of the present disclosure, the user interface includes a control; and the processor is configured to:

detect a heartbeat type input by a user via the control; and determine the heartbeat type input by the user as the currently triggered heartbeat type.

According to another aspect of the present disclosure, there is provided a system for amending a heartbeat type, including:

a processor; and a memory for storing instructions executable by the processor;

wherein the processor is configured to execute the instructions to:

display an interface for presenting heartbeat waveforms;

when detecting that at least one electrocardiogram waveform on the interface for presenting the heartbeat waveforms is selected, based on a user interface provided on the interface for presenting the heartbeat waveforms, detect a currently triggered heartbeat type; and amend a heartbeat type of the selected at least one electrocardiogram waveform as the currently triggered heartbeat type.

According to an implementation of the present disclosure, the user interface includes an icon for representing a heartbeat type; and the processor is further configured to:

detect an icon for representing a heartbeat type which is clicked by a user; and determine the heartbeat type corresponding to the icon as the currently triggered heartbeat type.

According to an implementation of the present disclosure, the processor is further configured to:

according to the currently triggered heartbeat type, store the selected at least one electrocardiogram waveform into a database associated with the currently triggered heartbeat type.

According to an implementation of the present disclosure, the user interface further includes an input window for inputting heartbeat feature values; and wherein the processor is further configured to:

detect a heartbeat feature value which is input into the input window by a user;

amend a heartbeat feature value which is preset for the currently triggered heartbeat type as the heartbeat feature value which is input by the user; and record the heartbeat feature value of the currently triggered heartbeat type as the amended heartbeat feature value.

According to an implementation of the present disclosure, the processor is further configured to:

determine whether a difference value between a heartbeat feature value of the selected at least one electrocardiogram waveform and a heartbeat feature value of the currently triggered heartbeat type is within a preset range; and if the difference value is within the preset range, amend the heartbeat type of the selected at least one electrocardiogram waveform as the currently triggered heartbeat type.

According to an implementation of the present disclosure, the processor is further configured to:

according to one of electrocardiogram waveforms which are currently selected and heartbeat types of which are amended, search other electrocardiogram waveforms which have the same heart beat feature value as that of the selected one on the interface for presenting heartbeat waveforms, and amend the heartbeat types of the other electrocardiogram waveforms as the currently triggered heartbeat type.

According to the methods for amending a heartbeat type provided by embodiments of the present disclosure, heartbeat types, heartbeat feature values and heartbeat colors of a plurality of electrocardiogram waveforms can be amended at a time. As compared with conventional technologies by which heartbeat types of electrocardiogram waveforms have to be amended one by one, the methods according to embodiments of the present disclosure can greatly improve the working efficiency of doctors, and save their working time. Particularly, when there are a huge number of electrocardiogram waveforms, significant increase in working efficiency can be achieved.

Further, by the methods for amending a heartbeat type provided by some embodiments of the present disclosure, at least one control for inputting heartbeat types is provided as a user interface. Thus, heartbeat types, heartbeat feature values and heartbeat colors of a plurality of electrocardiogram waveforms can be amended at a time.

By the methods for amending a heartbeat type provided by some embodiments of the present disclosure, icons for other heartbeat types are provided as a user interface, and a heartbeat feature value and a heartbeat color are assigned to each heartbeat type. Thus, heartbeat types, heartbeat feature values and heartbeat colors of a plurality of electrocardiogram waveforms can be amended at a time, and inputting of the heartbeat feature values and heartbeat colors corresponding to the triggered heartbeat types can be avoided.

By the methods for amending a heartbeat type provided by some embodiments of the present disclosure, heartbeat feature values are compared, and by the comparison between the feature values, more accurate results can be given out to help doctors to classify heartbeats. Thus, accuracy of the classification results can be improved.

By the methods for amending a heartbeat type provided by some embodiments of the present disclosure, a screening function for screening electrocardiogram waveforms having the same heartbeat type is provided, and thus electrocardiogram waveforms having the same waveform feature values as the electrocardiogram waveforms the heartbeat types of which have been amended can be automatically screened out and automatic batch amending can be realized. This can reduce repetitive judgment and amending of electrocardiogram waveforms having the same heartbeat type performed by doctors, and thereby can save the analysis time and greatly improve the working efficiency.

It should be understood that the above general description and the detailed description later are illustrative but not for limiting the scope of the present disclosure.

BRIEF DESCRIPTION OF THE DRAWINGS

The above and other objectives, features and advantages of the present disclosure will become more clear from the following description of exemplary embodiments with reference to the drawings.

DETAILED DESCRIPTION

Example implementations will be described in further detail with reference to the accompanying drawings. The example implementation, however, may be embodied in various forms, and should not be construed as being limited to the implementations described herein; instead, providing these implementations will make the present disclosure more comprehensive and complete and will fully convey the conception of the exemplary implementations to those skilled in this art. The drawings are only illustrative and are not depicted in proportion. Throughout the drawings, the like reference numbers refer to the same or the like structures, and repeated descriptions will be omitted.

The features, structures or characteristics described herein may be combined in one or more embodiments in any suitable manner. In the following descriptions, many specific details are provided to facilitate sufficient understanding of the embodiments of the present disclosure. However, those skilled in this art will appreciate that the technical solutions in the present disclosure may be practiced without one or more of the specific details, or by employing other methods, components, devices, steps, and so on. In other conditions, well-known structures, methods, devices, implementations, or operations are not shown or described in detail in order to avoid confusion of respective aspects of the present disclosure.

Figure 1:
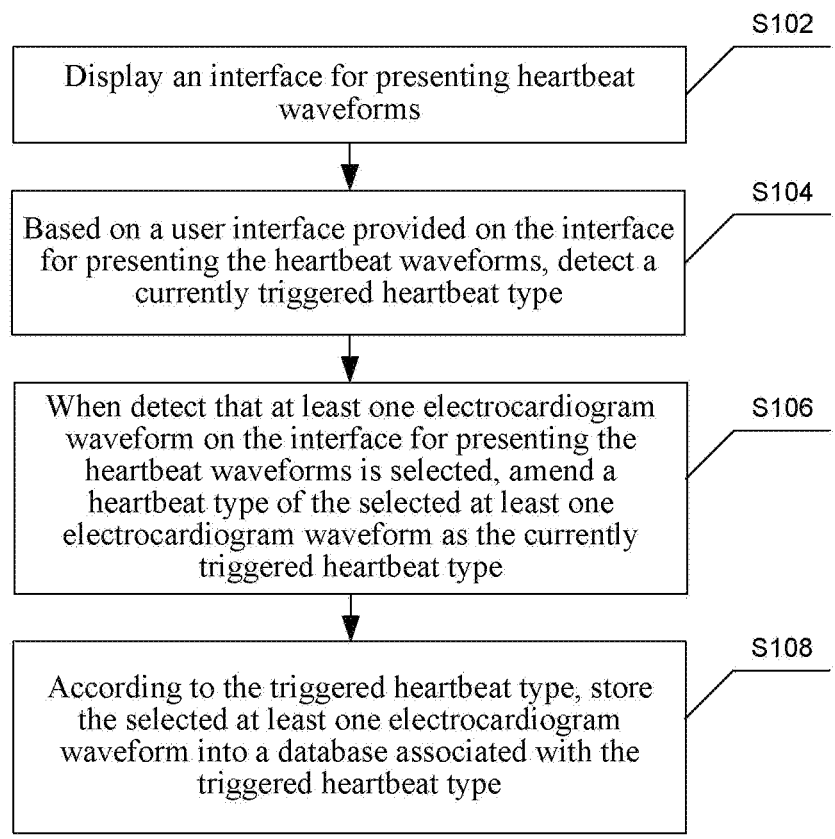
FIG. 1 is a flowchart showing a method for amending a heartbeat type according to an exemplary embodiment.

FIG. 1 is a flowchart showing a method for amending a heartbeat type according to an exemplary embodiment. As shown in FIG. 1, the method 10 may include the following steps.

In step S102, an interface for presenting heartbeat waveforms is displayed.

After an electrocardiogram data recorder samples electrocardiogram data, electrocardiogram data can be obtained from an ambulatory electrocardiogram recording box of the electrocardiogram data recorder according to a system instruction and a path indicated by the instruction.

Data analysis software analyzes the sampled electrocardiogram waveforms, and initially classifies the electrocardiogram waveforms. The data analysis software can make the initial classification on the electrocardiogram waveforms according to a preset classification standard, and the electrocardiogram waveforms can be classified into different heartbeat types. For example, the heartbeat types may include normal heartbeat, ventricular heartbeat, supraventricular heartbeat, pacing heartbeat, escape beat, interatrial block heartbeat, aberrant conduction heartbeat and artifact heartbeat, and the like. The preset classification standard may be feature values of P-QRS-T wave group on electrocardiogram waveforms.

After the initial classification on the sampled electrocardiogram waveforms is finished, an instruction from a user can be waited or detected. According to the detected user instruction, an interface for presenting heartbeat waveforms of one of the heartbeat types after the initial classification is displayed.

On the interface for presenting the heartbeat waveforms, all initially classified electrocardiogram waveforms of a corresponding heartbeat type are displayed, so that operators can amend electrocardiogram waveforms, the heartbeat types of which are incorrectly determined.

If the detected user instruction indicates that the user selects one heartbeat type after initial classification, electrocardiogram waveforms which are initially classified into the heartbeat type are displayed on the interface for presenting the heartbeat waveforms of the heartbeat type.

In step S104, based on a user interface provided on the interface for presenting the heartbeat waveforms, a currently triggered heartbeat type is detected.

On the interface for presenting the heartbeat waveforms of the heartbeat type which is selected by the user, a user interface can be provided. By the user interface, the user can trigger a heartbeat type which has predetermined heartbeat feature values and a heartbeat color.

The heartbeat feature values may include feature values of the P-QRS-T wave group on electrocardiogram waveforms, for example, the amplitude and the duration of the P wave: P-A and P-T; the amplitude and the duration of the QRS wave group: QRS-A and QRS-T; the amplitude and the duration of the T wave: T-A and T-T; PR intervals: PR; and QT intervals: QT, and the like.

The heartbeat color refers to a color corresponding to a heartbeat type. For example, white color may represent a normal heartbeat, red color may represent a ventricular heartbeat, pink color may represent supraventricular heartbeat, and so on. That is, each heartbeat type corresponds to a unique color. By the different colors, the heartbeat types can be distinguished conveniently and clearly, and users can intuitively and conveniently recognize data features when different colors are applied in other analysis such as histogram analysis and scatter diagram.

In step S106, when it is detected that at least one electrocardiogram waveform on the interface for presenting the heartbeat waveforms is selected, a heartbeat type of the selected at least one electrocardiogram waveform is amended as the currently triggered heartbeat type.

In this step, whether at least one electrocardiogram waveform on the interface for presenting the heartbeat waveforms of the user-selected heartbeat type is selected is detected. The selected electrocardiogram waveform may be continuous or not, and embodiments of the present disclosure do not impose specific limitations on this.

When at least one electrocardiogram waveform on the interface for presenting the heartbeat waveform is selected, the heartbeat type of the selected at least one electrocardiogram waveform is amended as the currently triggered heartbeat type.

In some embodiments, the method 10 may further include a step S108. In step S108, according to the currently triggered heartbeat type, the selected at least one electrocardiogram waveform is stored into a database associated with the currently triggered heartbeat type. The counted number of electrocardiogram waveforms of the currently triggered heartbeat type increases accordingly. In addition, an update function can be provided to the user. After the user clicks an update option, the selected at least one electrocardiogram waveform is removed from the interface for presenting the heartbeat waveforms of the heartbeat type selected by the user. Thus, the user has opportunity to perform amendments. In addition, when the interface for presenting heartbeat waveforms of the currently triggered heartbeat type is displayed, the electrocardiogram waveforms, the heartbeat types of which are updated, can be displayed as well.

According to the methods for amending a heartbeat type provided by embodiments of the present disclosure, heartbeat types, heartbeat feature values and heartbeat colors of a plurality of electrocardiogram waveforms can be amended at a time. As compared with conventional technologies by which heartbeat types of electrocardiogram waveforms have to be amended one by one, the methods according to embodiments of the present disclosure can greatly improve the working efficiency of doctors, and save their working time. Particularly, when there are a huge number of electrocardiogram waveforms, significant increase in working efficiency can be achieved.

It should be appreciated that how to implement and use particular examples are described in the present disclosure, but the principles of the present disclosure are not limited to the details of the exemplary examples. Instead, the principles of the present disclosure can be applied into any other implementations based on the teaching of the disclosure herein.

Figure 2:
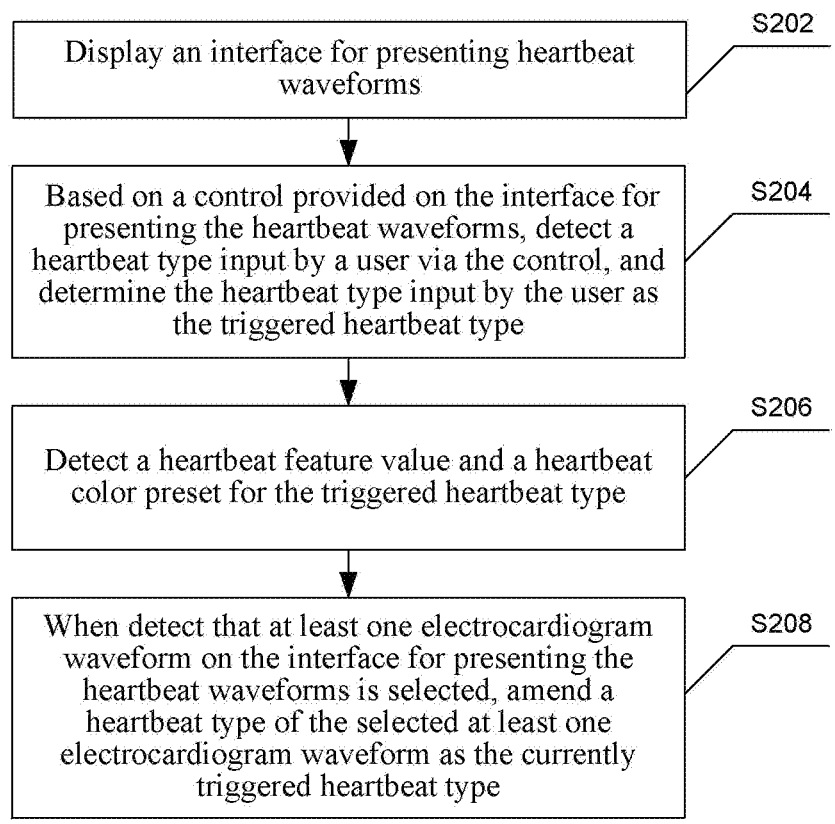
FIG. 2 is a flowchart showing a method for amending a heartbeat type according to an exemplary embodiment.

FIG. 2 is a flowchart showing a method for amending a heartbeat type according to an exemplary embodiment. As shown in FIG. 2, the method 20 may include the following steps.

In step S202, an interface for presenting heartbeat waveforms is displayed.

Details about step S202 can be found in the above descriptions with respect to step S102 in the method 10, and repeated descriptions are not provided here.

In step S204, based on a control provided on the interface for presenting the heartbeat waveforms, a heartbeat type input by a user via the control is detected, and the heartbeat type input by the user is determined as the currently triggered heartbeat type.

For example, a control may be provided on the interface for presenting heartbeat waveforms of a heartbeat type which is selected by the user from the heartbeat types after initial classification. The control is not limited to any particular type and may vary according to actual applications, and the present disclosure dose not impose specific limitations on this. The control allows users to input heartbeat types. For example, the control can provide pull-down menus for users to select or provide input windows for users to directly input heartbeat types. The detected heartbeat type which is input by the user can be taken as the (currently) triggered heartbeat type.

Further, after the user triggers the heartbeat type via the user interface, the currently triggered heartbeat type may be stored until the user triggers a new heartbeat type next time. Thus, for subsequently selected electrocardiogram waveforms, the heartbeat types of which need to be amended as the triggered heartbeat type, the user only need to trigger the heartbeat type for one time. By contrast, in conventional methods, doctors need to re-click or re-select a control every time when they amend the heartbeat type of an electrocardiogram waveform. The method provided by the present disclosure can simplify the operations of doctors.

In step S206, a heartbeat feature value or heartbeat feature values and a heartbeat color preset for the triggered heartbeat type are detected.

The heartbeat feature values may include feature values of the P-QRS-T wave group on electrocardiogram waveforms, for example, the amplitude and the duration of the P wave: P-A and P-T; the amplitude and the duration of the QRS wave group: QRS-A and QRS-T; the amplitude and the duration of the T wave: T-A and T-T; PR intervals: PR; and QT intervals: QT, and the like.

The heartbeat color refers to a color corresponding to a heartbeat type. For example, white color may represent a normal heartbeat, red color may represent a ventricular heartbeat, pink color may represent supraventricular heartbeat, and so on. That is, each heartbeat type corresponds to a unique color. By the different colors, the heartbeat types can be distinguished conveniently and clearly, and users can intuitively and conveniently recognize data features when different colors are applied in other analysis such as histogram analysis and scatter diagram.

After the heartbeat type is input, heartbeat types of subsequently selected electrocardiogram waveforms can be amended. That is, the heartbeat type only needs to be input for once, and there is no need to select the heartbeat type for each of the electrocardiogram waveforms, the heartbeat types of which need to be amended. In this way, working efficiency of doctors can be greatly improved, and working time can be saved. A heartbeat feature value (heartbeat feature values) and a heartbeat color are assigned to each heartbeat type in advance. Thus, if the heartbeat type is input by pull-down menus or direct input for example, the heartbeat feature value(s) and heartbeat color assigned to the heartbeat type can be obtained, without manual input by doctors.

In some embodiments, input window(s) for inputting heartbeat feature value(s) can be provided on the interface for presenting heartbeat waveforms, so that the heartbeat feature value(s) corresponding to the currently triggered heartbeat type can be amended. After the heartbeat type (i.e., the triggered heartbeat type) is input, the preset heartbeat feature value(s) corresponding to the triggered heartbeat type are displayed in the window for inputting heartbeat feature value(s). The preset values in the input window(s) may be amended or edited by a user according to actual requirements. After the user confirms the amendments, the system can re-detect all heartbeat feature values, assign the updated heartbeat feature value(s) to the triggered heartbeat type, and store and record the updated heartbeat feature value(s) to replace the preset heartbeat feature value(s). In practical clinic, many doctors employ different judgment standards according to specific individual differences between patients. For example, judgment standards for old people aged 60 or above are not applicable for children or young people aged 16 or below. Thus, doctors can set heartbeat feature values for different heartbeat types according to their clinical experiences, that is, they can set the thresholds for heartbeat types by themselves. The methods provided by the present disclosure allow users to amend the heartbeat feature values corresponding to a heartbeat type by themselves, and this can solve the problem that heartbeat cannot be accurately classified under a single judgment standard due to individual differences, and can therefore provide a fast and customized amending tool and guarantee the accuracy of ambulatory electrocardiogram examination. Some experienced doctors may determine a heartbeat type of a single electrocardiogram waveform not only by the shape of the single electrocardiogram waveform and the P-QRS-T feature values of the electrocardiogram waveform, and may also determine the heartbeat type with consideration of the heartbeat feature values of electrocardiogram waveforms before or after the electrocardiogram waveform. Under such condition, selected electrocardiogram waveforms near the thresholds may not be limited to the preset thresholds, so that the analysis results can comply with doctors' judgment and clinic usage habits better.

Further, when the heartbeat feature values corresponding to the triggered heartbeat type are amended, values can be assigned to the heartbeat features corresponding to the currently triggered heartbeat type according to the number of the selected heartbeat feature values. The number of the feature values of P-QRS-T on electrocardiogram waveforms is allowed to be defined by users, and users can select the number of heartbeat feature values, for example, users can select the feature values of QRS or the feature values of P and T and the like. A selection control can be provided before each heartbeat feature value, all the selection controls are ticked by default, and the heartbeat feature values under a ticked state are allowed to be amended. Every time when a selection is confirmed, detection of the selected feature values is performed for once, only the ticked heartbeat feature value item is assigned with the triggered heartbeat type, but all the heartbeat feature values are stored into a template library associated with the triggered heartbeat type. The manner for defining effective items by users is very helpful for doctors in clinical usage. In actual judgment procedure, depending on the shape variations of heartbeat types, some distinctive heartbeat types do not need to be defined by all of the P-QRS-T waveform feature values, and only one or two feature values are needed to determine the heartbeat type. Under such condition, allowing doctors to select effective items can effectively customize the screening items for heartbeat types, and effective feature values are only assigned to the heartbeat type corresponding to the selected icon. In this way, accuracy in classifying distinctive heartbeat types and efficiency in amending heartbeat types can be improved, thereby better complying with clinical use habits. Also, doctors are allowed to assign values for other features, and under such condition, only the heartbeat feature values and color corresponding to the selected icon are assigned to the heartbeat type corresponding to the selected icon. Such selection manner is more flexible, and therefore is more helpful for those experienced doctors.

In step S208, when it is detected that at least one electrocardiogram waveform on the interface for presenting the heartbeat waveforms is successively selected, a heartbeat type of the selected at least one electrocardiogram waveform is amended as the currently triggered heartbeat type.

Details about step S208 can be found in the above descriptions with respect to step S106 in the method 10, and repeated descriptions are not provided here.

In addition, the method 20 may further include the step S108 as described above with respect to the method 10, and details about step S108 are not repeated here.

According to the methods for amending a heartbeat type provided by embodiments of the present disclosure, a control for inputting heartbeat types is provided as a user interface, heartbeat types of a plurality of electrocardiogram waveforms can be amended at a time. As compared with conventional technologies by which heartbeat types of electrocardiogram waveforms have to be amended one by one, the methods according to embodiments of the present disclosure can greatly improve the working efficiency of doctors, and save their working time. Particularly, when there are a huge number of electrocardiogram waveforms, significant increase in working efficiency can be achieved.

Figure 3:
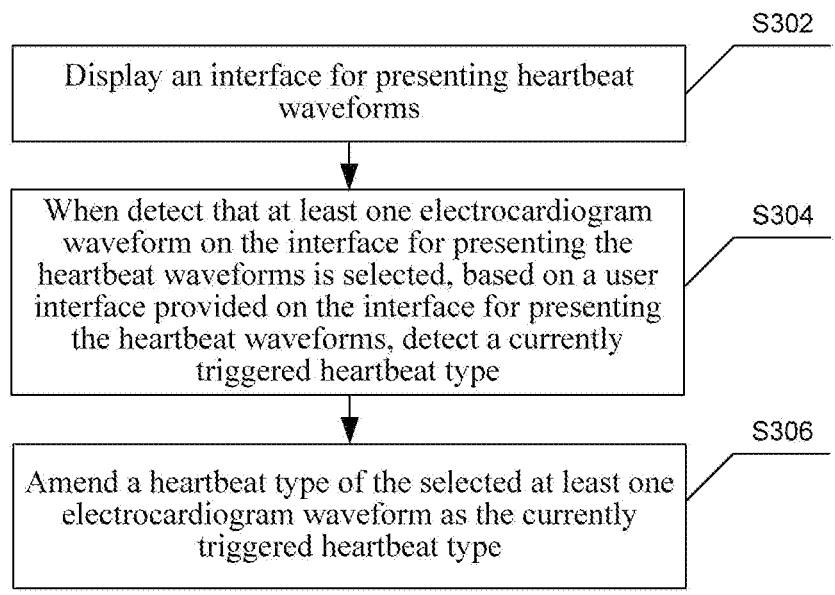
FIG. 3 is a flowchart showing a method for amending a heartbeat type according to an exemplary embodiment.

FIG. 3 is a flowchart showing a method for amending a heartbeat type according to an exemplary embodiment. As shown in FIG. 3, the method 30 may include the following steps.

In step S302, an interface for presenting heartbeat waveforms is displayed.

Details about step S302 can be found in the above descriptions with respect to step S102 in the method 10, and repeated descriptions are not provided here.

In step S304, when it is detected that at least one electrocardiogram waveform on the interface for presenting the heartbeat waveforms is selected, based on a user interface provided on the interface for presenting the heartbeat waveforms, a currently triggered heartbeat type is detected.

When it is detected that at least one electrocardiogram waveform on the interface for presenting the heartbeat waveforms is selected by a user, the currently triggered heartbeat type is detected via the user interface.

In some embodiments, the user interface may include an icon for representing a heartbeat type for example. If the user clicks the icon for representing a heartbeat type, the heartbeat type corresponding to the icon is determined as the currently triggered heartbeat type, and the heartbeat feature values preset for the heartbeat type corresponding to the icon are detected.

For example, on the interface for presenting heartbeat waveforms of one heartbeat type which is selected by the user from the heartbeat types after initial classification, icons for presenting other heartbeat types than the selected heartbeat type can be provided for the user to click or select. When clicking on an icon for a heartbeat type by the user is detected, the heartbeat type corresponding to the clicked icon is determined as the currently triggered heartbeat type.

Also, a heartbeat feature value (or heartbeat feature values) and a heartbeat color are preset for each heartbeat type, and once the user triggers the heartbeat type, the heartbeat feature(s) and heartbeat color preset and recorded for the heartbeat type are read.

The heartbeat feature values may include feature values of the P-QRS-T wave group on electrocardiogram waveforms, for example, the amplitude and the duration of the P wave: P-A and P-T; the amplitude and the duration of the QRS wave group: QRS-A and QRS-T; the amplitude and the duration of the T wave: T-A and T-T; PR intervals: PR; and QT intervals: QT, and the like.

The heartbeat color refers to a color corresponding to a heartbeat type. For example, white color may represent a normal heartbeat, red color may represent a ventricular heartbeat, pink color may represent supraventricular heartbeat, and so on. That is, each heartbeat type corresponds to a unique color. By the different colors, the heartbeat types can be distinguished conveniently and clearly, and users can intuitively and conveniently recognize data features when different colors are applied in other analysis such as histogram analysis and scatter diagram.

This method provides a more convenient icon click manner to trigger (or select) a heartbeat type, and uses the preset heartbeat feature values and heartbeat color to avoid inputting of the heartbeat feature values and heartbeat color corresponding to the heartbeat type, thereby further improving working efficiency of doctors.

In some embodiments, the control in the method 20 can be also provided on the interface for presenting heartbeat waveforms. Once the user clicks the icon for any heartbeat type, the heartbeat type and the heartbeat feature values and the heartbeat color corresponding to the heartbeat type are displayed on the input windows of the control for inputting the heartbeat type and the heartbeat feature values and the heartbeat color corresponding to the heartbeat type, so that users can view these values.

In some embodiments, input window(s) for inputting heartbeat feature value(s) can be provided on the interface for presenting heartbeat waveforms, so that the heartbeat feature value(s) corresponding to the currently triggered heartbeat type can be amended. After the heartbeat type (i.e., the triggered heartbeat type) is input, the preset heartbeat feature value(s) corresponding to the triggered heartbeat type are displayed in the window for inputting heartbeat feature value(s). The preset values in the input window(s) may be amended or edited by a user according to actual requirements. After the user confirms the amendments, the system can re-detect all heartbeat feature values, assign the updated heartbeat feature value(s) to the triggered heartbeat type, and store and record the updated heartbeat feature value(s) to replace the preset heartbeat feature value(s). In practical clinic, many doctors employ different judgment standards according to specific individual differences between patients. For example, judgment standards for old people aged 60 or above are not applicable for children or young people aged 16 or below. Thus, doctors can set heartbeat feature values for different heartbeat types according to their clinical experiences, that is, they can set the thresholds for heartbeat types by themselves. The methods provided by the present disclosure allow users to amend the heartbeat feature values corresponding to a heartbeat type by themselves, and this can solve the problem that heartbeat cannot be accurately classified under a single judgment standard due to individual differences, and can therefore provide a fast and customized amending tool and guarantee the accuracy of ambulatory electrocardiogram examination. Some experienced doctors may determine a heartbeat type of a single electrocardiogram waveform not only by the shape of the single electrocardiogram waveform and the P-QRS-T feature values of the electrocardiogram waveform, and may also determine the heartbeat type with consideration of the heartbeat feature values of electrocardiogram waveforms before or after the electrocardiogram waveform. Under such condition, selected electrocardiogram waveforms near the thresholds may not be limited to the preset thresholds, so that the analysis results can comply with doctors' judgment and clinic usage habits better.

Further, when the heartbeat feature values corresponding to the triggered heartbeat type are amended, values can be assigned to the heartbeat features corresponding to the heartbeat type triggered by the currently selected icon according to the number of the selected heartbeat feature values. The number of the feature values of P-QRS-T on electrocardiogram waveforms is allowed to be defined by users, and users can select the number of heartbeat feature values, for example, users can select the feature values of QRS or the feature values of P and T and the like. A selection control can be provided before each heartbeat feature value, all the selection controls are ticked by default, and the heartbeat feature values under a ticked state are allowed to be amended. Every time when a selection is confirmed, detection of the selected feature values is performed for once, only the ticked heartbeat feature value item is assigned with the triggered heartbeat type, but all the heartbeat feature values are stored into a template library associated with the triggered heartbeat type. The manner for defining effective items by users is very helpful for doctors in clinical usage. In actual judgment procedure, depending on the shape variations of heartbeat types, some distinctive heartbeat types do not need to be defined by all of the P-QRS-T waveform feature values, and only one or two feature values are needed to determine the heartbeat type. Under such condition, allowing doctors to select effective items can effectively customize the screening items for heartbeat types, and effective feature values are only assigned to the heartbeat type corresponding to the selected icon. In this way, accuracy in classifying distinctive heartbeat types and efficiency in amending heartbeat types can be improved, thereby better complying with clinical use habits. Also, doctors are allowed to assign values for other features, and under such condition, only the heartbeat feature values and color corresponding to the selected icon are assigned to the heartbeat type corresponding to the selected icon. Such selection manner is more flexible, and therefore is more helpful for those experienced doctors.

In step S306, a heartbeat type of the selected at least one electrocardiogram waveform is amended as the currently triggered heartbeat type.

Details about step S106 can be found in the above descriptions with respect to step S106 in the method 10, and repeated descriptions are not provided here.

In addition, the method 30 may further include the step S108 as described above with respect to the method 10, and details about step S108 are not repeated here.

According to the methods for amending a heartbeat type provided by embodiments of the present disclosure, icons for other heartbeat types are provided as user interfaces, and a heartbeat feature value (heart feature values) and a heartbeat color are assigned to each heartbeat type. Thus, heartbeat types, heartbeat feature values and heartbeat colors of a plurality of electrocardiogram waveforms can be amended at a time, and inputting of the heartbeat feature values and heartbeat colors corresponding to the triggered heartbeat types can be avoided. As compared with conventional technologies by which heartbeat types of electrocardiogram waveforms have to be amended one by one, the methods according to embodiments of the present disclosure can greatly improve the working efficiency of doctors, and save their working time. Particularly, when there are a huge number of electrocardiogram waveforms, significant increase in working efficiency can be achieved.

Figure 4:
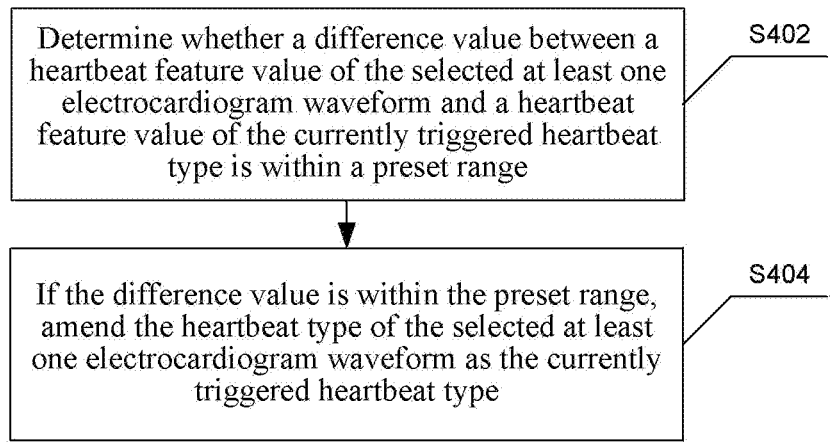
FIG. 4 is a flowchart showing a method for amending a heartbeat type according to an exemplary embodiment.

FIG. 4 is a flowchart showing a method for amending a heartbeat type according to an exemplary embodiment. On the basis of the above methods 10 to 30, the method 40 as shown in FIG. 4 further provide steps for determining whether to amending the heartbeat type of a selected electrocardiogram waveform. Specifically, the method 40 can include the following steps.

In step S402, whether a difference value between a heartbeat feature value of the selected at least one electrocardiogram waveform and a heartbeat feature value of the currently triggered heartbeat type is within a preset range is determined.

The preset range can be set depending on actual application requirements and embodiments of the present disclosure do not impose specific limitations on this.

In step S404, if the difference value is within the preset range, the heartbeat type of the selected at least one electrocardiogram waveform is amended as the currently triggered heartbeat type.

If the difference value is within the preset range, the heartbeat type of the selected at least one electrocardiogram waveform is allowed to be amended as the currently triggered heartbeat type.

If the difference value is outside the preset range, notification information may be provided for prompting the user if he/she wants to make amendments. If the user confirms to amend, the heartbeat type of the selected at least one electrocardiogram waveform is amended as the currently triggered heartbeat type; if the user cancels the amendments, the amendments are not allowed. This method allows doctors to perform selection more flexibly.

Successively selected feature values of P-QRS-T waves on the at least one electrocardiogram waveform are automatically obtained. The feature values of the P-QRS-T waves may include: P-A, P-T, QRS-A, QRS-T, T-A, T-T, PR and QT. Difference values between these obtained feature values and the feature values corresponding to the triggered heartbeat type are calculated, and whether the difference values are within a preset range is determined. This judgment method can effectively help doctors reduce judgment mistakes resulted from subjective judgment errors. When classifying different types of heartbeats, if a doctor is not sure about one selected electrocardiogram waveform, and he/she cannot determine whether the electrocardiogram waveform can be classified into the triggered heartbeat type only by recognizing the shape features of the electrocardiogram waveform, the comparison of the heartbeat feature values can help the doctor accurately define the judgment threshold of the triggered heartbeat type in numerical values, and for some electrocardiogram waveforms which are hard to determine, more accurate results can be given out by the comparison of feature values. Thus, this method can help doctors classify heartbeats, and thereby accuracy in classification results is improved.

Figure 5:
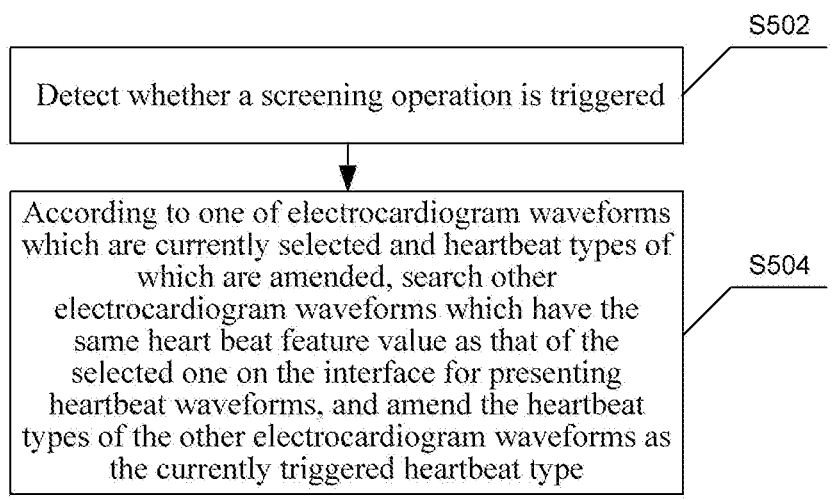
FIG. 5 is a flowchart showing a method for amending a heartbeat type according to an exemplary embodiment.

Further, FIG. 5 is a flowchart showing a method for amending a heartbeat type according to an exemplary embodiment. On the basis of the above methods 10 to 40, the method 50 as shown in FIG. 5 further provides a step for screening selected electrocardiogram waveforms. The method 50 can include the following steps.

In step S502, whether a screening operation is triggered is detected.

For example, a screening instruction from a user can be detected to determine whether the screening operation is triggered. The screening instruction may be an operation on a screening control provided on the interface, or may be a right button operation or other combination of operation on menus, and embodiments of the present disclosure do not impose specific limitations on this.

In step S504, according to one of electrocardiogram waveforms which are currently selected and heartbeat types of which are amended, other electrocardiogram waveforms which have the same heart beat feature value as that of the selected one on the interface for presenting heartbeat waveforms are searched, and the heartbeat types of the other electrocardiogram waveforms are amended as the currently triggered heartbeat type.

The screening function is provided on the current interface for presenting heartbeat waveforms. After the heartbeat type of the selected electrocardiogram waveform is amended, a screening operation can be started. If it is detected that the screening operation is triggered, with the feature values of P-QRS-T waves on the electrocardiogram waveform which is selected and the heartbeat type of which is amended as a screening condition (in other words, a query condition), all other electrocardiogram waveforms having the same heartbeat feature values as that of the selected electrocardiogram waveform are found out, and the heartbeat types of the other electrocardiogram waveforms can be amended as the triggered heartbeat type.

In addition, on the interface for presenting heartbeat waveforms, only the screened other electrocardiogram waveforms can be displayed.

By intensively displaying the screened other electrocardiogram waveforms, for example, arranged by rows, the other electrocardiogram waveforms which do not belong to the triggered heartbeat type are automatically blocked, and only the electrocardiogram waveforms which are in conformity with the condition(s) set for the triggered heartbeat type are displayed. This is very convenient for performing subsequent batch amending, updating the template type and the counted number corresponding to the triggered heartbeat type at the same time and giving out the latest numerical statistical results in real time. If a doctor amends one selected electrocardiogram waveform, it can be determined that the doctor considers that the heartbeat types of all electrocardiogram waveforms which have the same shape as that of the selected electrocardiogram waveform can be set as the same heartbeat type. In conventional amending methods, the doctor needs to view electrocardiogram waveforms one by one, and when similar heartbeats are found, the doctor needs to amend the heartbeat types of these found electrocardiogram waveforms one by one, and this undoubtedly causes repeated operations and lacks intelligence. By contrary, in the present disclosure, every time after the doctor amends one selected electrocardiogram waveform, electrocardiogram waveforms which have the same waveform feature vales as that of the selected electrocardiogram waveform are automatically screened out, with the feature values of the selected electrocardiogram waveform as a query condition. Thus, batch amending operation can be performed automatically. This can help doctors reduce repeated judgments and amendments on the electrocardiogram waveforms having the same heartbeat type, and thereby can reduce analysis time and greatly improve working efficiency.

One of ordinary skill in this art should appreciated that all or a part of the steps included in the above implementations can be realized by computer program instructions executable by CPU (Central Processing Unit). The computer program instructions are executed by the CPU to realize the above functions defined by the methods according to the present disclosure. The program instructions can be stored in a computer readable medium which can be a read only memory, a magnetic disk or an optical disk, or the like.

In addition, it should be noted that the drawings are described herein for illustrating the processes included in the methods according to exemplary embodiments of the present disclosure but not for limiting the scope of the present disclosure. It should be understood that the processes in these drawings are only illustrative and do not need to be performed based on the time sequence as illustrated in the drawings. It should be further understood that these processes can be executed in a plurality of modules synchronously or asynchronously.

Devices according to embodiments of the present disclosure, which can be configured to perform the methods according to embodiments of the present disclosure, will be described below. Details about the embodiments of devices can be found in the description with respect to the above embodiments of methods.

Figure 6:
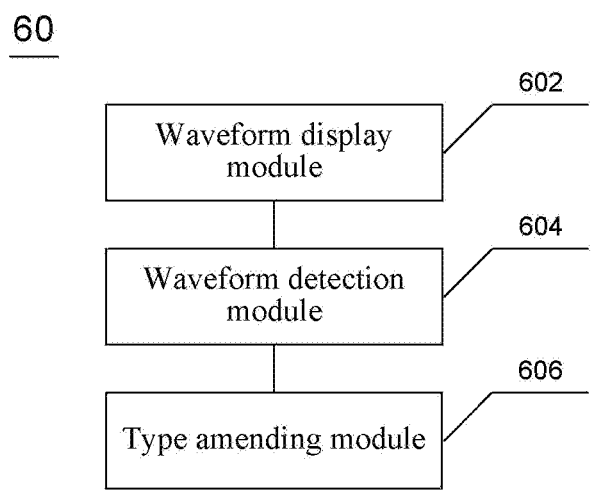
FIG. 6 is a block diagram showing a device for amending a heartbeat type according to an exemplary embodiment.

FIG. 6 is a block diagram of a device for amending a heartbeat type according to an exemplary embodiment. As shown in FIG. 6, the device 60 includes a waveform display module 602, a waveform detection module 604 and a type amending module 606.

The waveform display module 602 is configured to display an interface for presenting heartbeat waveforms.

The waveform detection module 604 is configured to, based on a user interface provided on the interface for presenting the heartbeat waveforms, detect a currently triggered heartbeat type.

In some embodiments, the user interface may include a control. The waveform detection module 604 includes a type detection sub-module and a type determination sub-module. The type detection sub-module is configured to detect a heartbeat type input by a user via the control. The type determination sub-module configured to determine the heartbeat type input by the user as the currently triggered heartbeat type.

The type amending module 606 is configured to, when it is detected that at least one electrocardiogram waveform on the interface for presenting the heartbeat waveforms is selected, amend a heartbeat type of the selected at least one electrocardiogram waveform as the currently triggered heartbeat type.

In some embodiments, the device 60 may further include a waveform storing module configured to, according to the currently triggered heartbeat type, store the selected at least one electrocardiogram waveform into a database associated with the currently triggered heartbeat type.

In some embodiments, the user interface may further include an input window for inputting heartbeat feature values. The device 60 may further include a window detection module, a feature value amending module and a feature value recording module. The window detection module is configured to detect a heartbeat feature value which is input into the input window by a user. The feature value amending module is configured to amend a heartbeat feature value which is preset for the currently triggered heartbeat type as the heartbeat feature value which is input by the user. The feature value recording module is configured to record the heartbeat feature value of the currently triggered heartbeat type as the amended heartbeat feature value.

In some embodiments, the device 60 may further include a feature value determination module configured to determine whether a difference value between a heartbeat feature value of the selected at least one electrocardiogram waveform and a heartbeat feature value of the currently triggered heartbeat type is within a preset range. The type amending module 606 is further configured to amend the heartbeat type of the selected at least one electrocardiogram waveform as the currently triggered heartbeat type if the difference is within the preset range.

In some embodiments, the device 60 may further include a waveform screening module configured to, according to one of electrocardiogram waveforms which are currently selected and heartbeat types of which are amended, search other electrocardiogram waveforms which have the same heart beat feature value as that of the selected one on the interface for presenting heartbeat waveforms, and amend the heartbeat types of the other electrocardiogram waveforms as the currently triggered heartbeat type.

Figure 7:
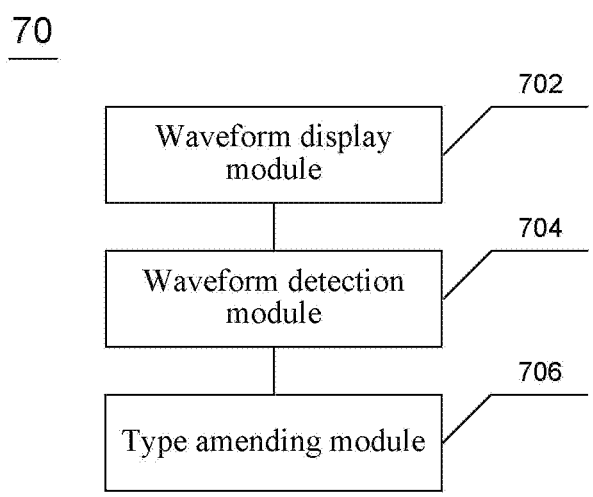
FIG. 7 is a block diagram showing a device for amending a heartbeat type according to an exemplary embodiment.

FIG. 7 is a block diagram of a device for amending a heartbeat type according to an exemplary embodiment. As shown in FIG. 7, the device 70 includes a waveform display module 702, a waveform detection module 704 and a type amending module 706.

The waveform display module 702 is configured to display an interface for presenting heartbeat waveforms.

The waveform detection module 704 is configured to, when it is detected that at least one electrocardiogram waveform on the interface for presenting the heartbeat waveforms is selected, based on a user interface provided on the interface for presenting the heartbeat waveforms, detect a currently triggered heartbeat type.

In some embodiments, the user interface may include an icon for representing a heartbeat type. The waveform detection module 704 may include a type detection sub-module and a type determination sub-module. The type detection sub-module is configured to detect an icon for representing a heartbeat type which is clicked by a user. The type determination sub-module is configured to determine the heartbeat type corresponding to the icon as the currently triggered heartbeat type.

The type amending module 706 is configured to amend a heartbeat type of the selected at least one electrocardiogram waveform as the currently triggered heartbeat type.

In some embodiments, the device 70 may further include a waveform storing module configured to, according to the currently triggered heartbeat type, store the selected at least one electrocardiogram waveform into a database associated with the currently triggered heartbeat type.

In some embodiments, the user interface may further include an input window for inputting heartbeat feature values. The device 70 may further include a window detection module, a feature value amending module and a feature value recording module. The window detection module is configured to detect a heartbeat feature value which is input into the input window by a user. The feature value amending module is configured to amend a heartbeat feature value which is preset for the currently triggered heartbeat type as the heartbeat feature value which is input by the user. The feature value recording module is configured to record the heartbeat feature value of the currently triggered heartbeat type as the amended heartbeat feature value.

In some embodiments, the device 70 may further include a feature value determination module configured to determine whether a difference value between a heartbeat feature value of the selected at least one electrocardiogram waveform and a heartbeat feature value of the currently triggered heartbeat type is within a preset range. The type amending module 706 is further configured to amend the heartbeat type of the selected at least one electrocardiogram waveform as the currently triggered heartbeat type if the difference value is within the preset range.

In some embodiments, the device 70 may further include a waveform screening module configured to, according to one of electrocardiogram waveforms which are currently selected and heartbeat types of which are amended, search other electrocardiogram waveforms which have the same heart beat feature value as that of the selected one on the interface for presenting heartbeat waveforms, and amend the heartbeat types of the other electrocardiogram waveforms as the currently triggered heartbeat type.

It should be appreciated that the blocks in the block diagrams are divided according to their functions but are not necessarily corresponding to entities which are independent physically or logically. The functional blocks (or entities) can be realized in software form, or can be realized by one or more hardware modules or integrated circuits, or can be realized in different networks and/or processors and/or microprocessors.

In view of the above description with respect to exemplary embodiments of the present disclosure, one or ordinary skill in this art can appreciate that the exemplary embodiments described herein can be realized by software, or by any appropriate combination of software and necessary hardware. Thus, the technical solutions according to embodiments of the present disclosure can be embodied as software products which can be stored in a non-volatile storage medium (for example, a CD-ROM, a USB flash drive, or a mobile hard disk drive, and the like) or stored over networks. The software products can include a plurality of instructions to cause a computing device (for example, a personal computer, a server, a mobile terminal, or a network device and the like) to execute the methods according to embodiments of the present disclosure.

The exemplary embodiments of the present disclosure are shown and explained above. It should be understood that the present disclosure is not limited to the specific structures, setting manners or implementations described herein; instead, the present disclosure is intended to encompass various modifications and equivalent settings without departing from the spirit and scope of the present disclosure.

What is claimed is:

1. A method for amending a heartbeat type, comprising:
   displaying an interface for presenting heartbeat waveforms;
   based on a user interface provided on the interface for presenting the heartbeat waveforms, detecting a currently triggered heartbeat type; and
   after the currently triggered heartbeat type is detected, selecting at least one electrocardiogram waveform on the interface for presenting the heartbeat waveforms, amending a heartbeat type of the selected at least one electrocardiogram waveform to be the currently triggered heartbeat type, wherein the heartbeat type of any selected electrocardiogram waveform is able to be amended to be the currently triggered heartbeat type, until a new triggered heartbeat type is determined;
   determining whether a difference value between a heartbeat feature value of the selected at least one electrocardiogram waveform and a heartbeat feature value of the currently triggered heartbeat type is within a preset range; and
   if the difference value is within the preset range, amending the heartbeat type of the selected at least one electrocardiogram waveform as the currently triggered heartbeat type;
   wherein the method further comprises:
   detecting whether a screening operation is triggered, and if the screening operation is triggered, according to one of electrocardiogram waveforms which are currently selected and heartbeat types of which are amended, searching other electrocardiogram waveform which have the same heart beat feature value as that of the selected one on the interface for presenting heartbeat waveforms, wherein each of the other electrocardiogram is a P-QRS-T wave, and amending the heartbeat types of the searched other electrocardiogram waveforms as the currently triggered heartbeat type, wherein the heartbeat type comprises a normal heartbeat, a ventricular heartbeat, a supraventricular heartbeat, a pacing heartbeat, an escape beat, an interatrial block heartbeat, an aberrant conduction heartbeat, and an artifact heartbeat.

2. The method according to claim 1, wherein the user interface comprises a control; and
   wherein the detecting the currently triggered heartbeat type comprises:
   detecting a heartbeat type input by a user via the control; and
   determining the heartbeat type input by the user as the currently triggered heartbeat type.

3. The method according to claim 1, further comprising:
   according to the currently triggered heartbeat type, storing the selected at least one electrocardiogram waveform into a database associated with the currently triggered heartbeat type.

4. The method according to claim 1, wherein the user interface further comprises an input window for inputting heartbeat feature values; and
   wherein the method further comprises:
   detecting a heartbeat feature value which is input into the input window by a user;
   amending a heartbeat feature value which is preset for the currently triggered heartbeat type as the heartbeat feature value which is input by the user; and
   recording the heartbeat feature value of the currently triggered heartbeat type as the amended heartbeat feature value.

5. The method according to claim 1, wherein the user interface comprises an icon for representing a heartbeat type; and
   the method further comprises:
   detecting an icon for representing a heartbeat type which is clicked by a user; and
   determining the heartbeat type corresponding to the icon as the currently triggered heartbeat type.

6. A system for amending a heartbeat type, comprising:
   a processor; and
   a memory for storing instructions executable by the processor;
   wherein the processor is configured to execute the instructions to:
   display an interface for presenting heartbeat waveforms;
   based on a user interface provided on the interface for presenting the heartbeat waveforms, detect a currently triggered heartbeat type; and
   after the currently triggered heartbeat type is detected, select at least one electrocardiogram waveform on the interface for presenting the heartbeat waveforms, amend a heartbeat type of the selected at least one electrocardiogram waveform to be the currently triggered heartbeat type, wherein the heartbeat type of any selected electrocardiogram waveform is able to be amended to be the currently triggered heartbeat type, until a new triggered heartbeat type is determined;

determine whether a difference value between a heartbeat feature value of the selected at least one electrocardiogram waveform and a heartbeat feature value of the currently triggered heartbeat type is within a preset range; and if the difference value is within the preset range, amend the heartbeat type of the selected at least one electrocardiogram waveform as the currently triggered heartbeat type;

detect whether a screening operation is triggered, and if the screening operation is triggered, according to one of electrocardiogram waveforms which are currently selected and heartbeat types of which are amended, search other electrocardiogram waveforms which have the same heart beat feature value as that of the selected one on the interface for presenting heartbeat waveforms, wherein each of the other electrocardiogram waveforms is a P-QRS-T wave, and amend the heartbeat types of the searched other electrocardiogram waveforms as the currently triggered heartbeat type, wherein the heartbeat type comprises a normal heartbeat, a ventricular heartbeat, a supraventricular heartbeat, a pacing heartbeat, an escape beat, an interatrial block heartbeat, an aberrant conduction heartbeat, and an artifact heartbeat.

7. The system according to claim 6, wherein the user interface comprises a control; and
the processor is configured to:
detect a heartbeat type input by a user via the control; and
determine the heartbeat type input by the user as the currently triggered heartbeat type.

8. The system according to claim 6, wherein the processor is further configured to:
according to the currently triggered heartbeat type, store the selected at least one electrocardiogram waveform into a database associated with the currently triggered heartbeat type.

9. The system according to claim 6, wherein the user interface further comprises an input window for inputting heartbeat feature values; and
wherein the processor is further configured to:
detect a heartbeat feature value which is input into the input window by a user;
amend a heartbeat feature value which is preset for the currently triggered heartbeat type as the heartbeat feature value which is input by the user; and
record the heartbeat feature value of the currently triggered heartbeat type as the amended heartbeat feature value.

10. A system for amending a heartbeat type, comprising:
a processor; and
a memory for storing instructions executable by the processor;
wherein the processor is configured to execute the instructions to:
display an interface for presenting heartbeat waveforms;
based on a user interface provided on the interface for presenting the heartbeat waveforms, detect a currently triggered heartbeat type; and
after the currently triggered heartbeat type is detected, select at least one electrocardiogram waveform on the interface for presenting the heartbeat waveforms is selected, and amend a heartbeat type of the selected at least one electrocardiogram waveform to be the currently triggered heartbeat type, wherein the heartbeat type of any selected electrocardiogram waveform is able to be amended to be the currently triggered heartbeat type, until a new triggered heartbeat type is determined;

determine whether a difference value between a heartbeat feature value of the selected at least one electrocardiogram waveform and a heartbeat feature value of the currently triggered heartbeat type is within a preset range; and if the difference value is within the preset range, amend the heartbeat type of the selected at least one electrocardiogram waveform and a heartbeat feature value of the currently triggered heartbeat type is within a preset range; and if the difference value is within the preset range, amend the heartbeat type of the selected at least one electrocardiogram waveform as the currently triggered heartbeat type;

detect whether a screening operation is triggered, and if the screening operation is triggered, according to one of electrocardiogram waveforms which are currently selected and heartbeat types of which are amended, search other electrocardiogram waveforms which have the same heart beat feature value as that of the selected one on the interface for presenting heartbeat waveforms, wherein each of the other electrocardiogram waveforms is a P-QRS-T wave, and amend the heartbeat types of the searched other electrocardiogram waveforms as the currently triggered heartbeat type, wherein the heartbeat type comprises a normal heartbeat, a ventricular heartbeat, a supraventricular heartbeat, a pacing heartbeat, an escape beat, an interatrial block heartbeat, an aberrant conduction heartbeat, and an artifact heartbeat.

11. The system according to claim 10, wherein the user interface comprises an icon for representing a heartbeat type; and
the processor is further configured to:
detect an icon for representing a heartbeat type which is clicked by a user; and
determine the heartbeat type corresponding to the icon as the currently triggered heartbeat type.

12. The system according to claim 10, wherein the user interface comprises a control; and
Wherein the processor is further configured to:
Detect a heartbeat type input by a user via the control; and
Determine the heartbeat type input by the user as the currently triggered heartbeat type.

13. The system according to claim 10, wherein the processor is further configured to:
according to the currently triggered heartbeat type, store the selected at least one electrocardiogram waveform into a database associated with the currently triggered heartbeat type.

14. The system according to claim 10, wherein the user interface further comprises an input window for inputting heartbeat feature values; and
wherein the processor is further configured to:
detect a heartbeat feature value which is input into the input window by a user;
amending a heartbeat feature value which is preset for the currently triggered heartbeat type as the heartbeat feature value which is input by the user; and
record the heartbeat feature value of the currently triggered heartbeat type as the amended heartbeat feature value.

* * * * *